United States Patent
Stumpe et al.

(10) Patent No.: US 12,367,691 B2
(45) Date of Patent: Jul. 22, 2025

(54) VIRTUAL STAINING FOR TISSUE SLIDE IMAGES

(71) Applicant: Verily Life Sciences LLC, South San Francisco, CA (US)

(72) Inventors: Martin Stumpe, Mountain View, CA (US); Philip Nelson, Mountain View, CA (US); Lily Peng, Mountain View, CA (US)

(73) Assignee: Verily Life Sciences LLC, Dallas, TX (US)

( * ) Notice: Subject to any disclaimer, the term of this patent is extended or adjusted under 35 U.S.C. 154(b) by 0 days.

(21) Appl. No.: 18/462,930

(22) Filed: Sep. 7, 2023

(65) Prior Publication Data
US 2023/0419694 A1    Dec. 28, 2023

Related U.S. Application Data (63) Continuation of application No. 16/958,555, filed as application No. PCT/US2018/021278 on Mar. 7, 2018, now Pat. No. 11,783,603.

(51) Int. Cl.
*G09G 5/02* (2006.01)
*G01N 1/30* (2006.01)
(Continued)

(52) U.S. Cl.
CPC ............... *G06V 20/69* (2022.01); *G01N 1/30* (2013.01); *G06F 18/214* (2023.01); *G06N 3/08* (2013.01);
(Continued)

(58) Field of Classification Search
CPC ...... G06V 20/69; G06V 10/82; G06V 20/695; G06V 2201/03; G06V 10/774; G01N 1/30;
(Continued)

(56) References Cited

U.S. PATENT DOCUMENTS 8,340,389 B2    12/2012    Kincaid
8,605,972 B2    12/2013    Yu et al.
(Continued)

FOREIGN PATENT DOCUMENTS

CN    102667473 A    9/2012
CN    107492090 A    12/2017
(Continued)

OTHER PUBLICATIONS

U.S. Appl. No. 16/958,555, "Final Office Action", Jan. 19, 2023, 10 pages.
(Continued)

*Primary Examiner* — Xin Jia
(74) *Attorney, Agent, or Firm* — Kilpatrick Townsend & Stockton LLP (57) ABSTRACT

A machine learning predictor model is trained to generate a prediction of the appearance of a tissue sample stained with a special stain such as an IHC stain from an input image that is either unstained or stained with H&E. Training data takes the form of thousands of pairs of precisely aligned images, one of which is an image of a tissue specimen stained with H&E or unstained, and the other of which is an image of the tissue specimen stained with the special stain. The model can be trained to predict special stain images for a multitude of different tissue types and special stain types, in use, an input image, e.g., an H&E image of a given tissue specimen at a particular magnification level is provided to the model and the model generates a prediction of the appearance of the tissue specimen as if it were stained with the special stain. The predicted image is provided to a user and displayed, e.g., on a pathology workstation.

19 Claims, 5 Drawing Sheets

(51) Int. Cl.

| | |
|---|---|
| *G06F 18/214* | (2023.01) |
| *G06N 3/08* | (2023.01) |
| *G06T 7/00* | (2017.01) |
| *G06T 11/00* | (2006.01) |
| *G06V 10/82* | (2022.01) |
| *G06V 20/69* | (2022.01) |
| *G16H 30/40* | (2018.01) |

(52) U.S. Cl.
CPC .......... *G06T 7/0012* (2013.01); *G06T 11/001* (2013.01); *G06V 10/82* (2022.01); *G06V 20/695* (2022.01); *G16H 30/40* (2018.01); *G01N 2001/302* (2013.01); *G06T 2207/20081* (2013.01); *G06T 2207/20084* (2013.01); *G06T 2207/30024* (2013.01); *G06T 2210/41* (2013.01); *G06V 2201/03* (2022.01)

(58) Field of Classification Search
CPC .. G01N 2001/302; G06F 18/214; G06N 3/08; G06N 3/045; G06N 3/0464; G06N 3/0475; G06N 3/0895; G06N 3/094; G06N 20/00; G06T 7/0012; G06T 11/001; G06T 2207/20081; G06T 2207/20084; G06T 2207/30024; G06T 2210/41; G16H 30/40
See application file for complete search history.

(56) References Cited

U.S. PATENT DOCUMENTS

| | | | |
|---|---|---|---|
| 8,639,013 | B2 | 1/2014 | Kenny |
| 8,725,237 | B2 | 5/2014 | Bryant-Greenwood et al. |
| 8,994,743 | B2 | 3/2015 | Young et al. |
| 9,002,077 | B2 | 4/2015 | Hoyt et al. |
| 9,697,582 | B2 | 7/2017 | Grunkin et al. |
| 9,785,818 | B2 | 10/2017 | Tieu et al. |
| 2005/0266395 | A1 | 12/2005 | Gholap et al. |
| 2014/0221813 | A1 | 8/2014 | Bryant-Greenwood et al. |
| 2014/0270457 | A1* | 9/2014 | Bhargava .............. G06V 20/69 382/133 |
| 2015/0269314 | A1 | 9/2015 | Kopriva et al. |
| 2017/0091937 | A1 | 3/2017 | Barnes et al. |
| 2017/0249548 | A1 | 8/2017 | Nelson et al. |
| 2019/0025773 | A1* | 1/2019 | Yang ...................... G06N 3/084 |
| 2019/0258984 | A1* | 8/2019 | Rehman ................ G06N 3/088 |
| 2020/0057069 | A1 | 2/2020 | Tajbakhsh et al. |

FOREIGN PATENT DOCUMENTS

| | | | | |
|---|---|---|---|---|
| EP | 3115766 | A1 | 1/2017 | |
| WO | 2010049651 | A1 | 5/2010 | |
| WO | 2013022688 | A1 | 2/2013 | |
| WO | WO-2015177268 | A1 * | 11/2015 | ......... G06K 9/00127 |
| WO | WO-2018052587 | A1 * | 3/2018 | ........... G06K 9/0014 |
| WO | WO-2018155898 | A1 * | 8/2018 | ............. G06N 20/00 |

OTHER PUBLICATIONS

U.S. Appl. No. 16/958,555, "Non-Final Office Action", Jun. 24, 2021, 17 pages.
U.S. Appl. No. 16/958,555, "Notice of Allowance", May 26, 2023, 8 pages.
Andersen et al., "Virtual Double Staining: A Digital Approach to Immunohistochemical Quantification of Estrogen Receptor Protein in Breast Carcinoma Specimens", Applied Immunohistochemistry & Molecular Morphology, vol. 26, No. 9, Oct. 2018, pp. 620-626.
Bentaieb et al., "Adversarial Stain Transfer for Histopathology Image Analysis", In Journal of IEEE Transactions on Medical Imaging, Dec. 8, 2017, 11 pages.
Bousmalis et al., "Unsupervised Pixel-Level Domain Adaptation with Generative Adversarial Networks", Available Online at: https://arxiv.org/pdf/1612.05424.pdf, Jul. 2017, pp. 95-109.
CN201880090874.7, "Notice of Decision to Grant", Jul. 12, 2023, 5 pages.
EP18713488.7, "Office Action", Nov. 16, 2022, 6 pages.
Giacomelli et al., "Virtual Hematoxylin and Eosin Transillumination Microscopy Using Epi-Fluorescence Imaging", Public Library of Science One, vol. 11, Issue 8, Aug. 8, 2016, pp. 1-13.
Mayerich et al., "Stain-Less Staining for Computed Histopathology", Technology, vol. 3, No. 1, Mar. 2015, pp. 1-11.
PCT/US2018/021278, "International Search Report and Written Opinion", Nov. 26, 2018, 12 pages.
Ronneberger et al., "U-Net: Convolutional Networks for Biomedical Image Segmentation", Computer Science Department and BIOSS Centre for Biological Signalling Studies, Available Online at: https://arxiv.org/pdf/1505.04597.pdf, May 18, 2015, pp. 1-8.
European Application No. 18713488.7, "Office Action", Nov. 13, 2024, 5 pages.

* cited by examiner

H&E (section 1)

Fig. 4B

IHC (adjacent section to 1)

Fig. 4C

H&E (section 3)

Fig. 4D

IHC (adjacent section to 3)

Input image (H&E)

Fig. 6B

Target image (IHC)

Fig. 6C

Predicted image (IHC)

VIRTUAL STAINING FOR TISSUE SLIDE IMAGES

CROSS REFERENCE TO RELATED APPLICATIONS

The present application is a continuation of U.S. patent application Ser. No. 16/958,555, filed Jun. 26, 2020, which is a U.S. national stage entry of PCT application serial no. PCT/US2018/021278 filed Mar. 7, 2018. The entireties of both of which are incorporated herein by reference.

BACKGROUND

This disclosure relates to a method of generating an artificial or virtual image of a tissue specimen having the appearance of being stained with a particular special staining chemical or chemicals, such as an immunohistochemical stain, from an input image of the tissue specimen. The input image could be an unstained image of the tissue specimen, or alternatively an image of the tissue specimen stained with a first stain, typically hematoxylin and eosin (H&E).

Histological tissue images are commonly stained with H&E to highlight tissue morphology, a procedure referred to as "routine staining". More specific stains, known in the art as "special stains" (e.g. immunohistochemical stains, IHCs) exist to highlight specific targets, e.g. very specific tumor markers, or cellular or tissue structures. Loosely speaking, this can be regarded as a very specific kind of image recoloring. Examples of special stains include HER2 stain for detecting specific genetic mutation markers in breast cancer specimens, PIN4, also known as "prostate triple stain" (P504S, HMW Keratins, P63) for prostate samples, Verhoeff's stain used in lung cancer tissue, and CK7 and AE1/AE3 cocktail stain for lymph node tissue.

Images of tissue specimens stained with special stains are relatively expensive to obtain due to the cost of the stains themselves (some of which are five times more expensive than an H&E stain), and labor and equipment costs. Additionally, often there is insufficient tissue available for all the stain images a pathologist may want to obtain to make a diagnosis, with normally each stain image requiring a separate slice of the tissue from a block of tissue. Obtaining further special stain images often takes significant additional time as well. Hence, in some circumstances it is desirable to obtain images of the specimen stained with many different IHC stains, e.g., in lung cancer, however it is either costly or potentially impossible to obtain such images without obtaining a further biopsy, or in any event cause a delay in coming to a diagnosis. The methods of this disclosure address, and preferably overcome, one or more of these limitations. We disclose how to generate virtual special stained images for a suite of special stains from an input image of the tissue specimen. The input image could be either unstained, or stained with the common H&E stain.

The method aims to have applications and benefits including one or more of (1) reducing the amount of actual staining required, and thereby lowering costs and eliminating additional delay in obtaining additional special stained images, (2) providing a preview to a pathologist of how an actual special stained image, or set of special stained images, might look like, for the pathologist to decide which ones they want to order, if necessary; and (3) providing visualizations and explanations to supplement other predictions, such as tumor detections, classifications, or predictions with respect to tissue samples.

The term "special stain" is defined in this document to mean stains other than hematoxylin and eosin (H&E) that are used to help visualize and/or identify structures and substances in biological specimens. These include, among others, immunohistochemical stains such as HER2 stain for detecting specific genetic mutation markers in breast cancer specimens, PIN4 and "prostate triple stain" (P504S, HMW Keratins, P63) for prostate samples, and CK7 stain for lymph node tissue, as well as other types of stains used in pathology including but not limited to acid fast stains for mycobacteria, Congo red for amyloid, Gram stains (various methods) for bacteria, Grocott's methenamine silver (GMS) for fungi, Jones methenamine silver for basement membrane and mesangium, Luxol fast blue-PAS for demyelination, Masson's trichrome for collagen & muscle, Periodic acid-Schiff (PAS), Phosphotungstic acid-hematoxylin (PTAH) for fibrin, Prussian blue for ferric iron, Sudan black for lipids & lipochrome pigments, Verhoeff's stain for elastin, and Warthin-Starry stain for bacteria.

SUMMARY

In general terms, we describe below a system for generating a machine learning predictor model which predicts a special stain image of a tissue sample. The system includes a) a data store containing a multitude of aligned pairs of images of tissue samples of a given tissue type, wherein each of the pairs consists of a first image of a tissue sample which is either unstained or stained with H&E (more generally, a "first stain") and a second image of the tissue sample which is stained with a second stain different from the first stain, and which is a typically a special stain; and b) a computer system configured as a machine learning predictor model trained from the multitude of aligned pairs of images in the data store to generate a predicted image of a tissue sample stained with the special stain from an input image of the type (Le. H&E stained, or unstained) of the first image in the pair of images and is of the given tissue type.

Note that the aligned pairs of images in the data store used for model are aligned closely or as precisely as possible; that is, they have an average distance between pairs of corresponding points in the respective images which is below a threshold, such as 1 or 2 pixels. For example, the threshold may be such that no more accurate alignment is possible with the alignment procedure that is used in practice.

A first specific expression of the disclosure is a system for generating a machine learning predictor model which predicts a special stain image of a tissue sample, comprising in combination:

a) a data store containing a multitude of aligned pairs of images of tissue samples of a given tissue type, wherein each of the pairs consists of a first image of a tissue sample which is either unstained or stained with H&E and a second image of the tissue sample which is stained with a special stain;

b) a computer system configured as a machine learning predictor model trained from the multitude of aligned pairs of images in the data store to generate a predicted image of a tissue sample stained with the special stain from an input image of the type (stained, unstained) of the first image in the pairs of images and which is of the given tissue type In one configuration, the special stain is in the form of an IHC stain, a variety of which are mentioned in this document. It may be any one (or more) of HER2, PIN4 or "prostate triple stain" (P504S, HMW Keratins, P63), Verhoeff's stain, and CK7 stain. The particular special stain may depend on the tissue type. In one configuration the given tissue type is one of the following types: breast tissue, prostate tissue, lymph node tissue, and lung tissue.

In one possible embodiment, the data store contains a multitude of pairs of images of different tissue types and different special stain types. Such a collection of image data can be either acquired from one or more public or private sources, or curated specially for development of the predictor model. The computer system implements different machine learning predictor models for each of the different tissue types and stain types.

Examples of machine learning predictor models that are suitable for the present purposes include generative adversarial networks, self-supervised learning neural networks, convolutional neural networks, and convolutional neural networks for dense segmentation, e.g., a convolutional neural network known as "U-Net."

In another aspect, a computer system is disclosed comprising one or more processing units and memory implementing one or more (or more preferably a plurality: "a suite") of machine learning predictor models, the models generating data in the form of a prediction of the appearance of a virtual special stained image of a tissue sample of a respective given tissue type from data representing an input unstained or H&E stained image of the given tissue sample.

In still another aspect, a method is provided for generating a virtual image of a tissue specimen stained with a special stain, comprising the steps of:
 obtaining an input image;
 supplying the input image to a machine learning predictor model trained from a multitude of pairs of aligned images of tissue specimens, one of the images of the pair of images comprising an image of a tissue specimen stained with the special stain, the model trained to predict an image of a tissue specimen stained with the special stain;
 with the predictor model, generating a predicted image of the tissue specimen stained with the special stain, and displaying the predicted image as the virtual image.

In one possible arrangement, the input image is an image of the tissue specimen in an unstained condition. Alternatively, the input image is an image of the tissue specimen stained with H&E. The special stain can take the form of any of the commercially available IHC stains. The tissue specimen can be one of several possible types, including breast tissue, prostate tissue, lymph node tissue and lung tissue.

In still another aspect, a method is disclosed of training a machine learning predictor model. The method includes a step a) of obtaining a multitude of pairs of aligned images of a tissue sample of a given tissue type, wherein each of the pairs consists of a first image of a tissue sample which is either unstained or stained with H&E and a second image of the tissue sample which is stained with a special stain; and a step b) of providing the multitude of pairs of aligned images as training data for a machine learning predictor model, the model learning to predict an image of a tissue sample stained with the special stain from an input image of the type (stained, unstained) of the first image in the pairs of images and is of the given tissue type.

The disclosure further provides, for each of the methods defined above, a respective computer program product (e.g. a tangible, machine-readable recording medium, but it may also be software downloadable over a communications network) storing program instructions which when implemented by a processor cause the processor to carry out the method. The disclosure further provides, for each computer program product, a respective computer system comprising a processor and a memory storing the computer program product.

BRIEF DESCRIPTION OF THE DRAWINGS

FIGS. 6A-6C are three different images of a tissue specimen.

DETAILED DESCRIPTION

As noted above, the methods of this disclosure provide for generation of a virtual stained image of a tissue specimen showing the appearance of the specimen as if it were stained with a special stain such as an IHC stain, from an input image which may be either an unstained image or an image of a specimen stained with H&E.

Figure 1:
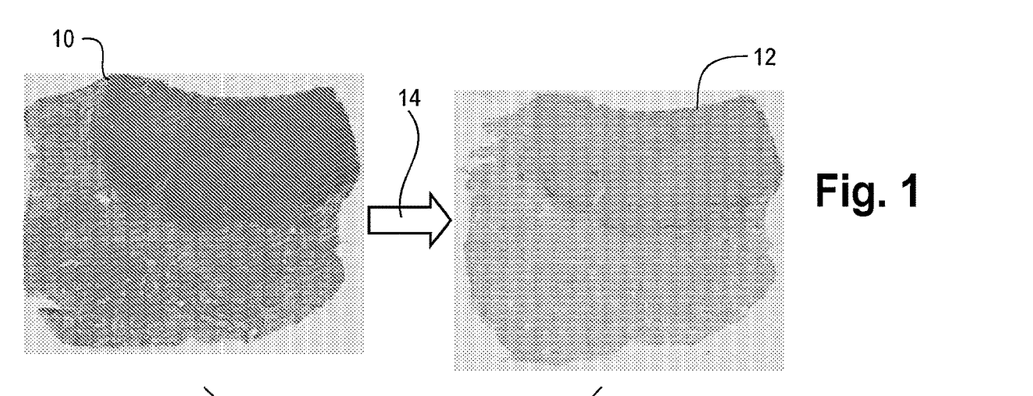
FIG. 1 is an illustration of a low magnification, whole slide image of a tissue specimen stained with H&E and a virtual or artificial image of the tissue specimen showing how it would appear if stained with an IHC stain.

As an example, FIG. 1 is an illustration of a low magnification, whole slide image 10 of a tissue specimen stained with H&E and a virtual or artificial image 12 of the tissue specimen showing how it would appear if stained with a special stain, in this case the IHC stain CD3. The arrow 14 indicates that a trained machine learning predictor model, described below, receives as input the whole slide image 10 and predicts the appearance of the virtual image 12. The predicted image is displayed for a user, for example on the display of a workstation used by a pathologist.

Figure 2:
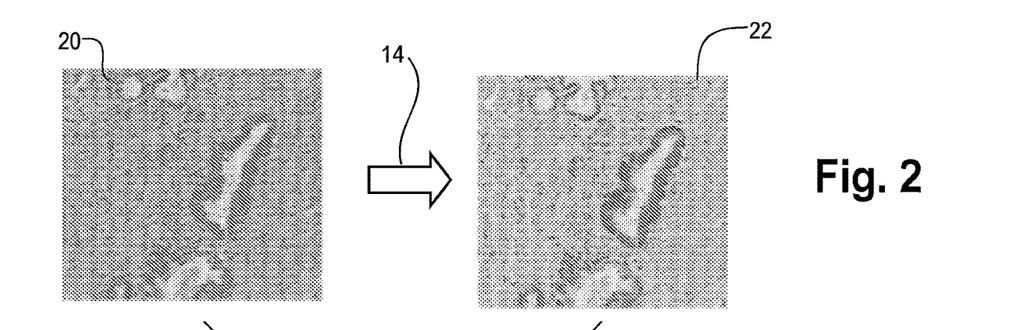
FIG. 2 is an illustration of a high magnification image of a tissue specimen stained with H&E and a virtual image of the same specimen showing how it would appear if stained with an IHC stain.

The training of the machine learning predictor model can occur at different magnification levels, for example low magnification (e.g., 5 or 10×), medium magnification (e.g. 20×) and at high magnification, such as 40×. Accordingly, the model can predict special stained images from either low, medium or high magnification input images. FIG. 2 is an illustration of a high magnification image 20 of a prostate tissue specimen stained with H&E and a virtual image 22 of the same specimen showing how it would appear if stained with an IHC stain, in this case the PIN4 special stain.

We will describe in detail below two aspects of how such virtual stain images are predicted: 1) generating and training a machine learning predictor model to predict a special stained image from an input image, and 2) after training, use of the trained predictor model to generate virtual stained images from input images.

Training

Our training procedure involves collecting a multitude, e.g., thousands, of pairs of images of the same tissue sample in various types of tissues, e.g., prostate, lung, breast etc., with one of the pairs of images being a special stained image of the tissue sample.

The image pairs could be, for example
(1) an unstained image and a special stained image, e.g. an IHC image, of the same tissue specimen, and/or
(2) an H&E image and a special stained image of the same tissue specimen. The image pairs are then precisely aligned with respect to each other and used as training data to train a machine learning predictor model to predict a special stained image from an input image.

Such pairs of images could be obtained from sequential tissue specimens from a tissue block or from a single tissue specimen that is either unstained, imaged and then special stained and imaged or, a single tissue specimen stained with H&E, de-stained, and then re-stained with a special stain.

Figure 3:
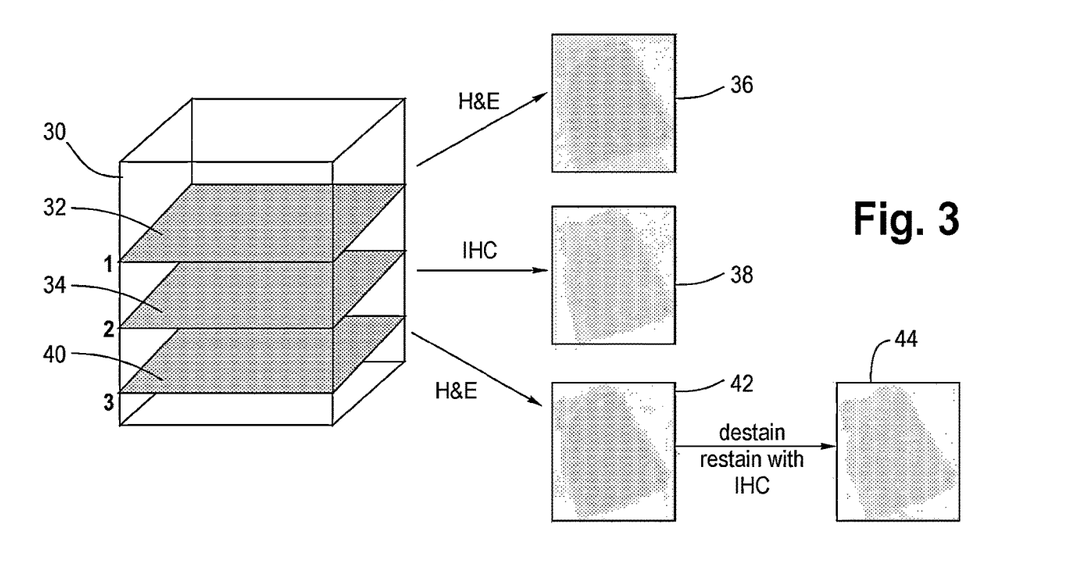
FIG. 3 is an illustration of several possible approaches for obtaining tissue sections from a block of tissue in order to generate training images for training a machine learning predictor model.

FIG. 3 shows a formalin fixed paraffin embedded tissue block 30, in which serial (adjacent) sections of the tissue block are cut with a microtome and placed on glass slides as is customary in the art. In one possible implementation, a first section 32 is stained with H&E. A second section 34, adjacent to the first section 32, is stained with an IHC or other special stain. The sections 32 and 34 after staining are subject to whole slide imaging with a conventional high resolution RGB whole slide scanner at different magnifications, such as 5×, 10×, 20× and 40×. This procedure results in images 36 and 38, where image 36 is say a 10× H&E stained image of the specimen and image 38 is a 10× IHC stained image of the specimen, the images at other magnifications are not shown.

An alternative is to take a section such as third section 40 of the tissue block, stain it with H&E, scan it with a whole slide scanner at different magnifications, resulting in a set of images, one of which is shown at 42, and then de-stain the specimen and then re-stain the specimen with an IHC or other special stain and generate a new set of images of the specimen with the IHC stain at different magnifications, one of which is shown at 44. Methods for de-staining, restaining and imaging tissue specimens are described in PCT application serial no. PCT/US18/13353 filed Jan. 11, 2018, the description of which is incorporated by reference herein.

Figure 4A:
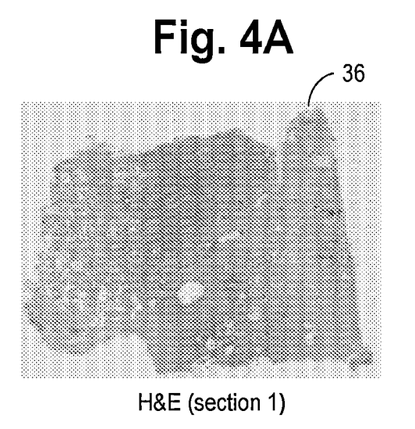
FIGS. 4A-4D are a set of images obtained from using the approaches shown in FIG. 3.
Figure 4B:
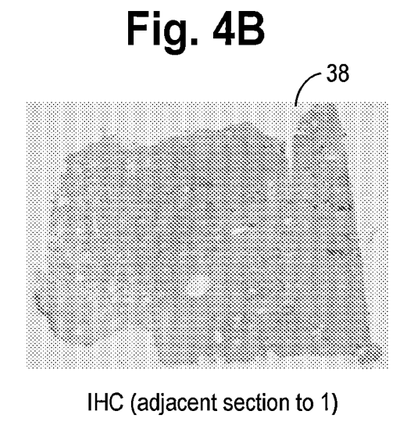
Figure 4C:
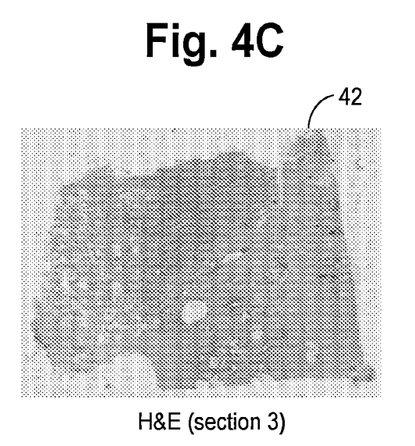
Figure 4D:
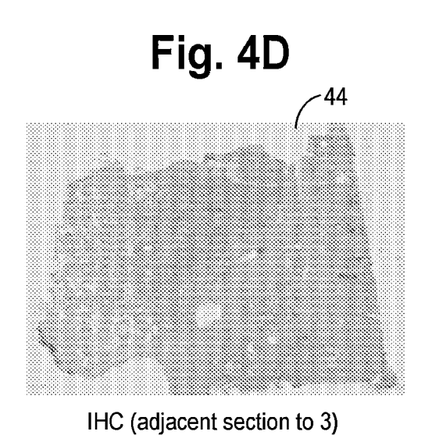

While FIG. 3 shows an initial step of staining a tissue sample with H&E, the methodology described below can be performed for unstained images in which case one section of the tissue block is removed, imaged at various magnifications in an unstained condition, then stained with a special stain, and then imaged at the same magnifications. It is possible to repeat this process for several different sections of the tissue block and apply different special stains to the sections in order to build up a set of image pairs (unstained/stained) with different special stains. Likewise, the procedure of FIG. 3 can be repeated so as to generate sets of H&E/special stain image pairs for different special stains. FIG. 4A-4D shows more detailed sets of images generated from the procedure of FIG. 3, in which FIG. 4A is an image 36 of the H&E stained specimen from the first section 32, FIG. 4B is the IHC image 38 from the adjacent second section 34, FIG. 4C is the H&E stained image 42 from section 40, and FIG. 4D is the re-stained IHC image 44 from section 3 (40). The images of FIGS. 4A and 48 could form one pair of images that could be used for model training. Similarly, the images of FIGS. 4C and 4D could be considered another pair of images used for model training. Additionally, the images of FIGS. 4C and 48 could be considered another pair of images used for model training.

The model training procedure will be described in greater detail below in conjunction with FIG. 7 using the pairs of images generated from the procedure of FIG. 3. It will be noted that the process of acquiring and aligning pairs of images will be performed many times, perhaps thousands of times, so as to build up a large training set of image pairs. Very accurate alignment of the image pairs should be performed such that the precisely aligned images are used during model training. This alignment could include warping of the images to make sure that cellular details are aligned despite potential tissue deformations between the images. By using re-staining of a single tissue sample (FIG. 3 and FIGS. 4C and 4D, images 42, 44) one can obtain very precisely aligned images provided the tissue sample is not disturbed substantially during re-staining.

Figure 5:
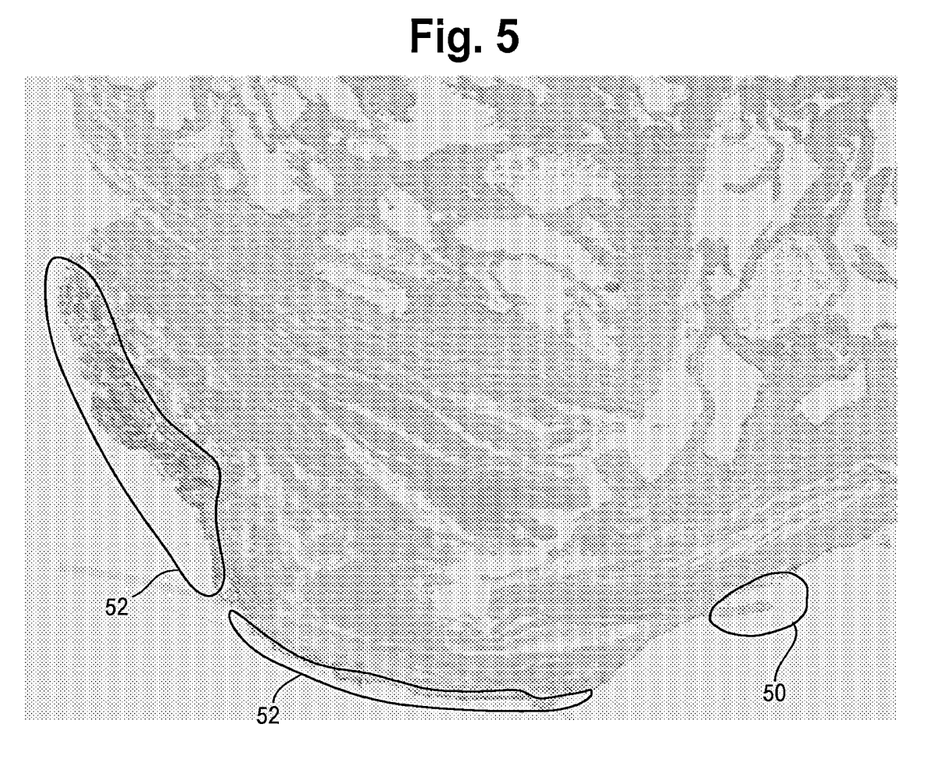
FIG. 5 is a low magnification image of a tissue specimen showing certain edge effects which may be present in training images. In one embodiment, the portion of the training images containing edges of tissue are not used in model training in order to avoid improper training of the model due to such edge effects.

FIG. 5 is a low magnification image of a tissue specimen showing certain edge effects which may be present in training images and which should be removed, i.e., not considered, during model training. The region 50 shows a tear in the edge of the tissue which is present in the image of FIG. 5 and this tear may be unique to the tissue specimen shown in FIG. 5, I.e., not present in an adjacent tissue section. The tear occurred as a consequence of handling the specimen during placement of the specimen on the slide, on staining the slide, or placing a cover slip on the slide. This tear may not be present in an image from an adjacent section of the tissue block, and hence the use of the image data in this region (and the image from the adjacent section of the tissue block without the tear) could adversely affect the learning or training of the machine learning predictor model. Tearing is not the only possible physical edge effect or discrepancy between adjacent sections. The delicate tissue samples can sometimes have deformations or damage at the edges, leading to local discrepancies between otherwise similar images. In more drastic cases these can be in the form of tissue ruptures or tissue folds. Even if instructions are given to laboratory technicians to proceed with extra caution and minimize these artifacts when sectioning, staining and imaging specimens to build up the training image data, some artifacts might still remain. Another potential undesired artifact at the tissue edge is ink, which is sometimes used in the lab to indicate where a tissue block is supposed to be sectioned. In FIG. 5, the regions 52 contain ink residues from such markings. The ink residue may or may not be present in an adjacent section, but its presence is undesirable and can adversely affect the model training. Accordingly, in one embodiment, edges of tissue sections are not used in model training in order to avoid improper training of the model due to such edge effects. The definition of "edge" that is used to exclude some portion of the image data from model training can take several possible forms, such as a minimum number of pixels away of boundaries between tissue and vacant areas of the slide.

Figure 6A:
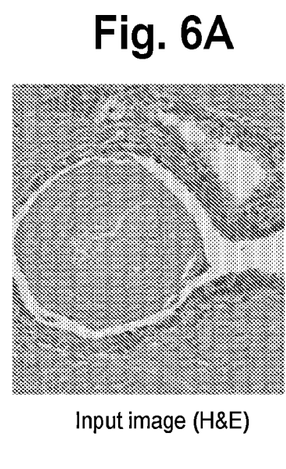
FIG. 6A is an H&E stained input image.
Figure 6B:
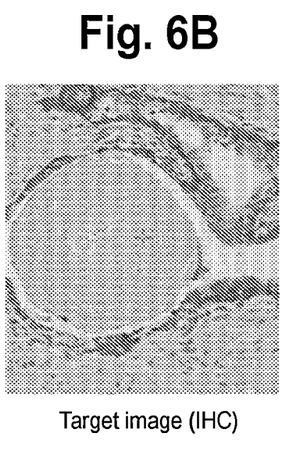
FIG. 6B is an actual IHC stained image of the tissue specimen shown in FIG. 6A.
Figure 6C:
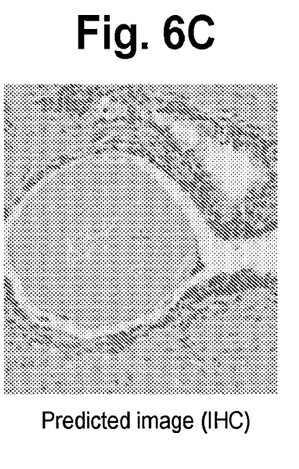
FIG. 6C is a virtual IHG-stained image for the tissue specimen shown in FIG. 6A which is predicted by the machine learning predictor model.
Figure 7:
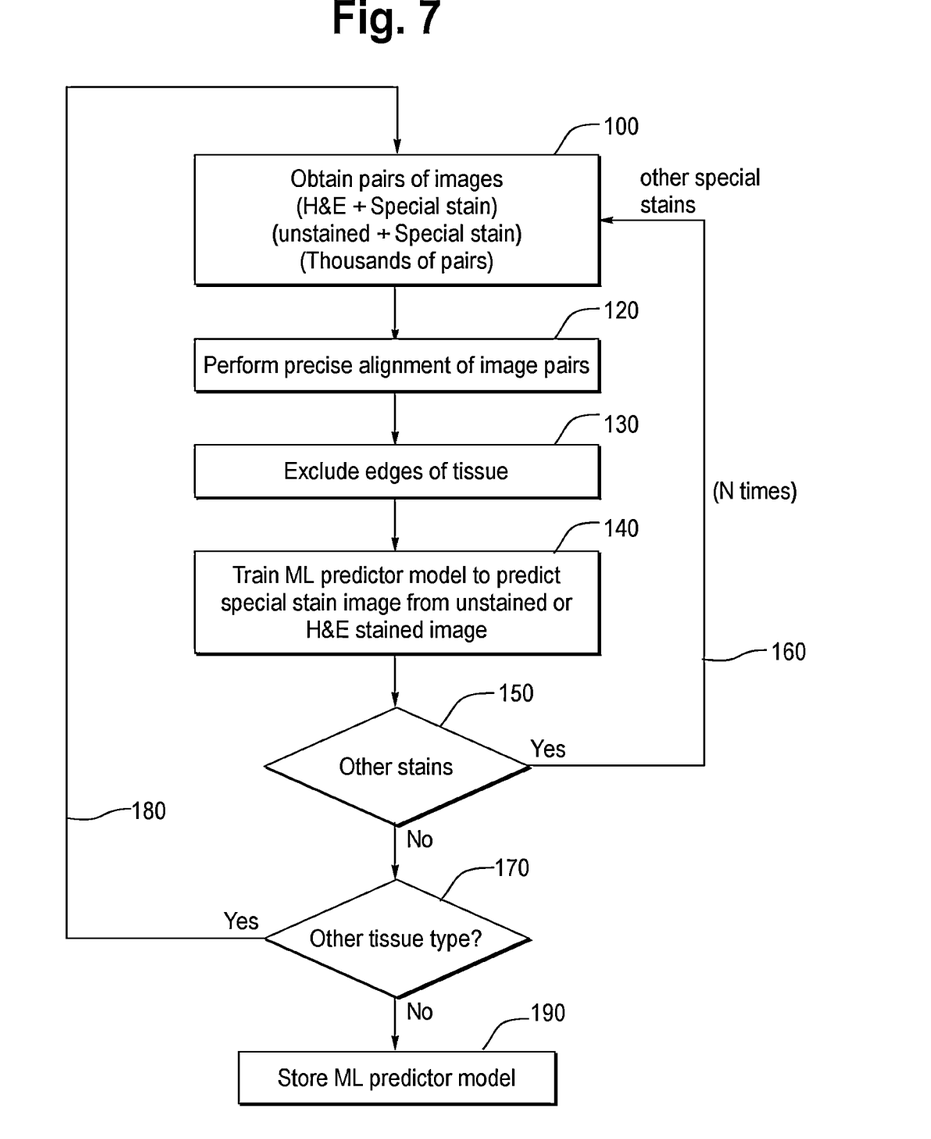
FIG. 7 is a flow chart showing a model training procedure for training a machine learning predictor model to predict special stained images from input pairs of images. The input pairs of images could take the form of unstained image+special stained image, or stained image (typically, H&E stained image)+special stained image. The process of FIG. 7 is repeated for different types of special stain images and different types of tissues in order to build up a suite or complex of machine learning predictor models to generate virtual stained images of a multitude of tissue and stain types.

Once model training according to FIG. 7 has occurred, the performance of the model can be assessed, e.g., by comparison of predicted images generated by the model with actual special stained images of a given tissue sample. For example, FIGS. 6A-6C are three different images of a prostate tissue specimen: FIG. 6A is an H&E stained input image, FIG. 68 is an actual IHC (PIN4) stained image of the tissue specimen shown in FIG. 6A, and FIG. 6C is a virtual IHC-stained (PIN4) image for the input tissue specimen image shown in FIG. 6A which is predicted by the machine learning predictor model. While the image of FIG. 6C is not exactly the same as the actual IHC image of FIG. 68, it is sufficiently close that a pathologist considering FIG. 6C can get a reasonable estimate of what a PIN4 (an IHC) image of the specimen shown in FIG. 6A would look like and as such is in a more informed position to determine whether or not to order a PIN4 stain image of the patient's tissue specimen. The virtual image of FIG. 6C may also be used for other purposes, such as providing visualizations of the tissue specimen and supporting explanations to supplement predictions made about the tissue specimen, such as tumor detections, diagnosis or classification of the tissue sample.

Model training will now be described in conjunction with FIG. 7. In the present discussion we will focus on a multitude (thousands) of pairs of tissue images for model training of a given type, such as breast cancer tissue, with one image being an H&E image of the specimen and the other image being a HER2 (special stained) image of the same specimen. The process for training is identical for other types of pairs of images, e.g., of different tissue types, of different stains, etc., or the situation where the first image in the pair of images is an unstained image.

In the model training process of FIG. 7, we start at step 100 with obtaining a multitude (e.g., thousands) of pairs of images of a given tissue type, such as for example images of breast cancer tissue. The image pairs could be unstained+ special stained, or stained (e.g., H&E stained)+special stained. Such pairs of images could be obtained from one or more private or publicly available pre-existing tissue image databases, or alternatively could be curated specially for a model training exercise from thousands of individual tissue specimens. Ideally, the pairs of images are provided in a variety of different magnifications in order to train the machine learning predictor model to predict special stained images at different magnifications of an input image. In the curated collection of images situation, thousands of tissue specimens of a given tissue type of patients in a variety of health conditions are obtained from public or private tissue collections, and the specimens are sectioned, stained, and then imaged in pairs as explained in conjunction with the discussion of FIGS. 3 and 4 at different magnifications.

At step 120, the multitude of pairs of images are precisely aligned or registered with respect to each other. Procedures for aligning or reregistering pairs of images to each other are known and described in the literature, see for example D. Mueller et al., *Real-time deformable registration of multimodal whole slides for digital pathology*, Computerized Medical Imaging and Graphics vol. 35 p. 542-556 (2011); F. EI-Gamal et al., *Current trends in medical image registration and fusion*, Egyptian Informatics Journal vol. 17 p. 99-124 (2016); J. Singla et al., *A systematic way of affine transformation using image registration*, International Journal of Information Technology and Knowledge Management, July-December 2012, Vol. 5, No. 2, pp. 239-243; Z. Hossein-Nejad et al., *An adaptive image registration method based on SIFT features and RANSAC transform*, Computers and electrical engineering Vol. 62 p. 5240537 (August 2017); U.S. Pat. Nos. 8,605,972 and 9,785,818, the descriptions of which are incorporated by reference herein. Since the training data for the virtual staining model will be pairs of (almost) identical image patches of H&E vs. special stain (or unstained vs. special stain) the images need to be aligned as perfectly as possible. With whole slide image sizes of 100,000×100,000 pixels and potentially local tissue deformations, the registration is not a trivial task of an affine transform but more likely requires some local warping as well. One possible approach is to perform a coarse global matching via rotation and transformation on a thumbnail level, and then match pairs of image patches. The method uses off the shelf image processing features combined with RANSAC (random sample consensus, a known algorithm for image alignment, see https://en.wikipedia.org/wiki/Random sample consensus and the Hossein-Nej ad paper) to do the alignment. Moreover, this method can handle the cases like patches that cannot be matched (e.g. because of tissue damage in one image but not the other).

At step 130, edge regions of the tissue images are masked and pixel values in such mask regions are nulled to as to exclude such edge regions from model training for the reasons explained previously.

At step 140, the precisely aligned pairs of images are supplied as training data to a machine learning predictor model. The training data is used to teach the model to predict a virtual stained image (in this example, a HER2 image) from the first or input image (the H&E image). For gigapixel images like microscopic tissue images, this predictor model would likely not operate (i.e., learn) on entire images at once, but instead learns on small patches of the images one at a time, or potentially on the images pixel-by-pixel. Alternatively, based on morphology or contrast values, the predictor model could operate on individual cells—that is identify individual cells in the input (H&E) image and learn to predict the corresponding IHC image of the cells. Pixel-to-pixel, cell-to-cell or patch-to-patch mapping is performed using the pairs of training images. Given two corresponding slides, any dense prediction algorithm should be able to perform the mapping with something like an L2 loss.

Some machine learning predictor models that would be very suitable candidates for this disclosure include:

1) Generative Adversarial Networks (GANs). This neural network approach is described in the article of K. Bousmalis, et al., *Unsupervised Pixel-Level Domain Adaptation with Generative Adversarial Networks*, https://arxiv.org/pdf/1612.05424.pdf (August 2017), the content of which is incorporated by reference herein. The present problem can be treating as a domain adaptation algorithm where one is trying to remap images from the source domain to look as if they came from the target domain. Persons skilled in the art would scale up the state-of-the art model described in the Bousmalis et al. paper to much larger images (such as gigapixel pathology images) and apply it to semantic segmentation on large scale datasets.

2) Self-supervised learning neural network (e.g. a model trained to predict parts of an 20 image when other parts of the image are shown).
3) Convolutional neural network, a broad class of neural networks used in computer vision problems and well described in the scientific literature.
4) Convolutional neural network for dense segmentation (e.g. U-Net). See the paper of O. Ronneberger et al., *U-Net: Convolutional Networks for Biomedical Image Segmentation*, https://arxiv.or J/abs/1505.04597 (2015), the content of which is incorporated by reference.

This training takes advantage of the property that the model is able to pick up subtle details or morphological features that are in the first image, but are not easy to pick up by a human. The input to the model is an RGB image, and the output is an RGB image with the same tissue morphology but different colors and contrast patterns, depending on the respective special stain that is predicted. Given that IHCs bind to very specific antigens and are indicators of local protein expressions (e.g. HER2 in the case of a ERBB2 breast cancer mutation), it is not a priori clear at all that the H&E image even contains the information to make a realistic prediction about the IHC image. The underlying assumption is that there is a causation or correlation between the morphological features in the tissue, and the local protein expression patterns. There is evidence that suggests this prediction might be possible: firstly, in related work the assignee of the present invention has succeeded in predicting a fluorescent cell microscopy images from brightfield grayscale images with very high accuracy, and secondly pathologists have confirmed that they can often detect subtle tumor features in an H&E image after seeing the corresponding IHC image—even though they initially missed those features in the H&E before seeing the IHC image. This confirms that there is subtle information in the H&E images that is easily missed by a human eye. However, the model training of this disclosure encodes or fixes the ability of a machine learning predictor model to identify such information and use it to generate virtual stain images.

Provided a large enough set of training data is available, the machine learning predictor model learns to predict an IHC image from an H&E image for a given tissue sample and IHC stain type, in this example breast cancer and HER2 stain.

At step 150, it is possible to train on the same tissue type but different special stain type. If this training is desired, for example to increase the generalizability and utility of the predictor model, then the process loops back as indicated at 160 to step 100 and obtains a set of image pairs, with one of them being of this second special stain type. For example, where it is customary to employ 4 different types of special stains for prostate cancer tissue samples, in a first iteration through loop 160 IHC stain #1 is used as the second image in the pair of images at step 100, and in the second iteration through the loop 160 IHC stain #2 is used as the second image in the pair of images at the second iteration at step 100, in a third iteration stain IHC #3 is used as the second image in the pair of images at step 100, and in a fourth iteration IHC stain #4 is used as the second image in the pair of images at step 100. Additional loops through procedure indicated at step 160 are also possible in the event it is desired to train the model to predict special stained images from unstained images, in which case the first image in the pair of images at step 100 is an unstained image, and the second image is a special stained image. If one desires to train the model over different stains for the given tissue type for unstained images, N loops through step 160 are taken for N different types of stains, where N is some integer greater than or equal to 2.

In practice, the looping indicated at 160 could result in a single model which can be used for multiple special stains (e.g. by the output layer comprising a different 2-D array of outputs for each respective special stain, so that the same hidden layers are used to generate multiple images at the output layer). Alternatively, each iteration through the loop 160 could result in a separate model, one per special stain type, where each model is defined by a distinct set of parameters, constants, etc.

At step 170, if it is desired to train the predictor model in different tissue types, the process loops back to step 100 as indicated at 180 and steps 100, 120, 130, 140, 150, and 160 are repeated as needed to train the predictor model for other tissue types, and possibly other different special stains for such tissue type or for unstained images as input at step 100, indicated by performing loop 160 one or more times. For example, it may be desired to create and train a suite of machine learning predictor models, one for each of a multitude of tissue types. Depending on the potential demand or uses of the system trained in accordance with FIG. 7 it is possible and desirable to train predictor models for all the various types of tissues and stains used in contemporary pathology practice, provided that tissue samples can be obtained and precisely aligned pairs of training images can be obtained such that the methodology of FIG. 7 can be implemented.

Once all the tissue types have been obtained and loop 180 has been executed as needed, at step 170 the no branch is taken and then the machine learning predictor models generated in accordance with FIG. 7 are stored in a computer system. The precise configuration of the predictor models, e.g., as a collection of model parameters, constants, executable code, algorithms, etc., will vary depending on the selection of model type as explained above, as will be understood by persons skilled in the art.

Furthermore, as explained above, the model training can be performed at different magnification levels of the pairs of images, e.g. 10×, 20× and 40×. Hence, the procedure of FIG. 7 may be executed multiple times for different magnification levels of the input image pairs at step 100. In particular, additional loops through the training procedure of FIG. 7 may also be performed for different magnification levels of the first and second images in the pair of images, for example at 5×, 10×, 20× and 40×, for each of the types of special stains, and for each of the types of tissues. In one possible configuration, a given machine learning predictor model can cope with predicting special stain images for an input image at all levels of magnification, but it would also be possible to train different models, one for each magnification.

Use

Once the machine learning predictor model(s) is/are trained, as per FIG. 7, an input image of the type for which the model is trained is supplied to the model and it generates a predicted or virtual special stained image that corresponds to that input image. In this example, if the model is trained to predict a HER2 image of breast cancer issue from an input H&E image of breast cancer tissue at 20×, the model predicts the HER2 image for the input image at 20×. The predicted image is then displayed to the user.

Figure 8:
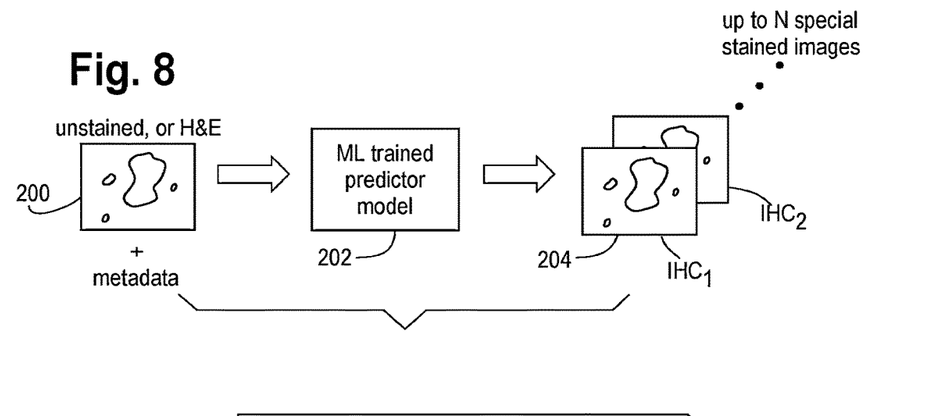
FIG. 8 is a flow chart showing a process of using a machine learning predictor model trained in accordance with FIG. 7.

As one example, with reference to FIG. 8 a pathologist obtains a specimen of breast tissue, and then has it sectioned and stained with H&E, scanned with a whole slide scanner, and then receives a whole slide image 200 of the tissue stained with H&E. The image can be associated with metadata, such as the patient identification, tissue type, stain type, magnification level, etc. The pathologist wants to see what a HER2 or other special stained image of the specimen might look like. Through simple user interface tools on a workstation they direct the input of the H&E image to the trained machine learning predictor model 202, and the model returns the predicted special stain image 204 which is then displayed on the workstation. The virtual stained image could be displayed also as an overlay on the H&E stained image of the specimen, for example in a mode where the user views the H&E stained image and activates an icon on the workstation display to switch between different virtual stains, essentially recoloring the H&E image into the respective stain image.

As another example, the model 202 is trained from H&E stained lung cancer tissue specimens and corresponding special stained images of the same tissue specimens in four different staining protocols or regimes (N=4), such as a suite of images of the tissue specimen stained with four different special stains. In use, a pathologist considering an H&E stained image 200 of a lung specimen supplies the image to the model 202 and it returns four different virtual stain images of the lung specimen stained with the suite of four different special stains 204. The pathologist consults the four virtual stain images 204 and decides to order one of the special stain images for the lung specimen. Alternatively, based on the quality of the virtual stain images 204, and comparison of the special stained images with the H&E stained image 200, the pathologist determines that the specimen is non-cancerous and does not order any special stains images for the lung specimen. The virtual stained images are appended to a diagnostic pathology report prepared by the pathologist.

Figure 9:
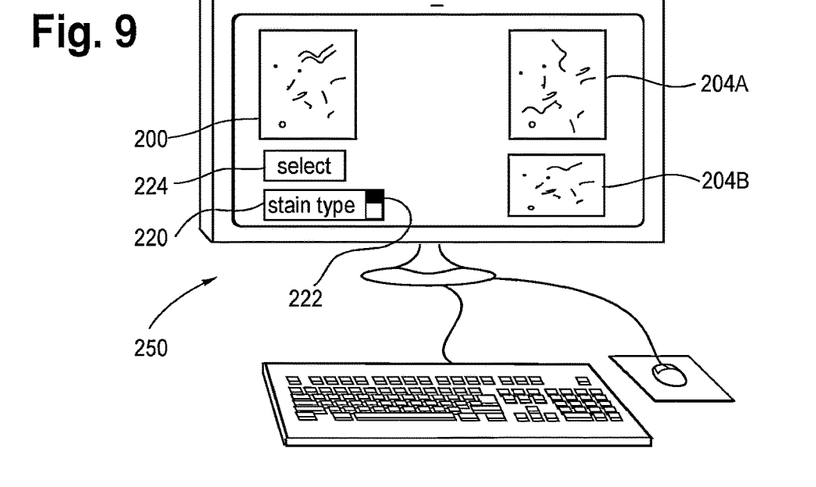
FIG. 9 is an illustration of a workstation used by a pathologist with simple user interface tools to select a tissue image to view on the workstation, and to select one or more virtual special stain images which are predicted by the machine learning predictor model and then displayed on the workstation.

FIG. 9 shows an example of a pathology workstation in which an input image 200 is shown displayed on the workstation 250 display. A tool 220 lists various different types of virtual stain images which are available for viewing of the particular sample type. The user navigates to different stain types by using the scroll bar 222. When they have navigated to a particular stain type that they want to see they activate the select icon 224 and a virtual stained image of that stain type is shown on the display. In this instance two stain types have been selected and the corresponding virtual stain images are shown at 204A and 204B. The virtual stained images can be shown side by side or superimposed on the original input image 200. This image 200 could be an unstained image or a stained image, e.g., stained with H&E, depending on how the model was trained using the procedure of FIG. 7.

Figure 10:
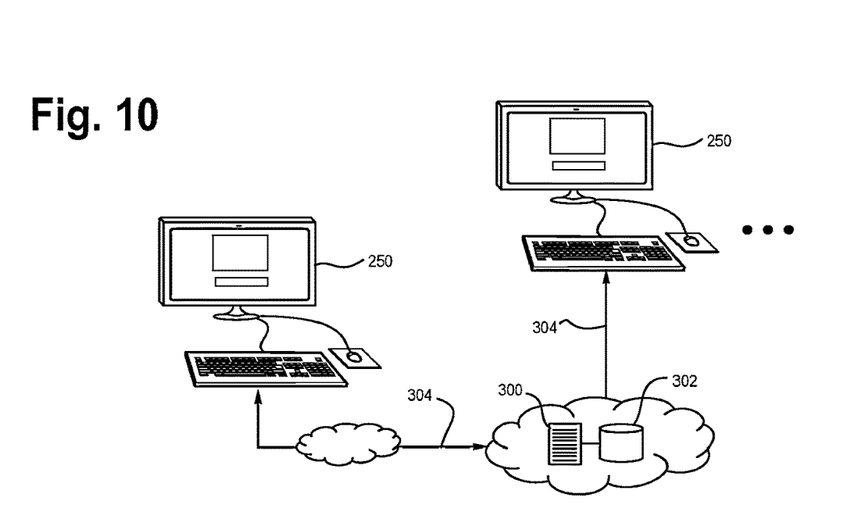
FIG. 10 is a block diagram showing a computing environment in which the methods of this disclosure can be practiced.

FIG. 10 shows one possible computing environment in which the methods of this disclosure can be practiced. A computer system 300 (which can take a variety of forms including specially programmed GPUs implementing the machine learning predictor models, servers, or other subsystems) is in communication with a data store 302 which stores pairs of images of tissue specimens in order to conduct model training as per FIG. 7. The computer 300 is provided with processors which execute software instructions implementing the machine learning model(s) including model parameters, algorithms, etc. In use, via an application programming interface, the user operating the workstations 250 selects input images locally from memory or data stores local to the workstation and the images along with associated metadata, e.g., indicating tissue type, are provided over computer networks 304 to the computer system 300 implementing the machine learning predictor model(s). The trained predictor model applicable to the tissue type for the input image then predicts the special stained image desired by the user of the workstation (specified in the metadata or as special instructions via the API). The predicted virtual special stained image is then provided over the network 304 and then displayed on the workstation 250. The computer system 300 may be operated as a fee-for-service or in some other business model.

Aside from the significant scientific breakthrough represented by the present disclosure, the ability to predict IHC stains from H&E stained images will have substantial impact on clinical diagnosis. In particular:

1. Cost savings—The cost for each IHC stain is currently on the order of $50. With large numbers of IHC stains being done per year in the US alone, this amounts to a total spending per year that is truly vast Being able to do even only a few types of IHC stains virtually instead of actually would therefore have the potential to save the health care industry (and patients) significant sums of money.
2. Increasing access—Some labs and clinics do not have the capability of performing IHC stains. If they need to be done, they are outsourced and hence incur additional latency.

The virtual staining could be done with almost no latency after the H&E stain has been performed and in facilities that do not have IHC capability.

3. Tissue availability—Tissue is often scarce, and pathologists often have to decide on which IHC stains they want to use the available tissue for. This is particularly the case for biopsies where tissue is very limited, e.g. in lung biopsies. With virtual stains, the number of potentially relevant stains to take into account for a case diagnosis would not be limited by tissue availability.
4. Real stain prioritization—Even if the actual real staining will still be performed, the prediction of how the stain will look likely could be useful in prioritizing which stains would be most valuable.
5. Enriching our ML training set—The virtual stain images generated in accordance with the methods of this disclosure can constitute additional training data for developing classification models.
6. Shorten turnaround time. Ordering an IHC image often delays the final time to diagnosis by a day or so. The present technology could shorten that time by either (i) not requiring the actual physical stained IHC image, or (2) providing relevant information upfront to decide whether an actual physical IHC stained image should be ordered or not.

One may ask about the usefulness of a virtual stained image. It can be argued that if the H&E image contains enough signal to predict how an IHC stain on this tissue would look like, we could as well predict the diagnosis right away and skip the "visualization" of the virtual IHC image. However, even if this is possible, there are significant advantages of producing the virtual IHC image over only the H&E image for diagnosis.

In particular:

1. Due to human fallibility, the reliability of the identification of the presence of certain conditions will be improved if the individual who performs it uses the virtual stained image, compared to an unstained/H&E stained image.
2. Explainability—the importance of showing pathologists the visualization of the stain that leads to the diagnosis can hardly be overestimated. It helps to establish trust in the methodology of this disclosure as well as any particular predictions that accompany the virtual stain image. This is especially strong if we can overlay the virtual IHC with the actual H&E images or an unstained image of the tissue sample.

3. Morphological information—the morphology of a tumor and its microenvironment is an important signal in diagnosis. Information such as the tumor size, structure and spatial relation of glands, or the location of invading lymphocytes contribute directly to the diagnosis and consideration of treatment options. All this spatial information would be lost in a purely classification prediction without stain visualization.

Privacy Considerations

All of the images that are used with model training are patient de-identified. Ethics review and institutional review board exemption is obtained from each institution from which the training images are obtained. If the training images are obtained from tissue blocks ethics review and institutional review board exemption is obtained from each institution providing the tissue blocks and such blocks are patient de-identified. Patient data was not linked to any Google user data. Furthermore, our system includes a sandboxing infrastructure that keeps each image dataset separated from each other, in accordance with regulation, data license and/or data use agreements. The data in each sandbox is encrypted; all data access is controlled on an individual level, logged, and audited.

The invention claimed is:

1. A method, comprising:
   obtaining an input red-green-blue ("RGB") image of a tissue specimen;
   supplying the input RGB image to a machine learning predictor model trained from a multitude of pairs of aligned RGB images of tissue specimens, one of the RGB images of the pair of RGB images comprising an RGB image of a tissue specimen stained with a special stain, the model trained to predict an RGB image of a tissue specimen stained with the special stain;
   with the predictor model, generating a predicted RGB image of the tissue specimen stained with the special stain; and
   outputting the predicted RGB image as a virtual RGB image.

2. The method of claim 1, wherein the input RGB image comprises an image of the tissue specimen in an unstained condition.

3. The method of claim 1, wherein the input RGB image comprises an image of the tissue specimen stained with routine stain.

4. The method of claim 1, wherein the special stain comprises an IHC stain.

5. The method of claim 1, wherein the tissue specimen is of one of the following types: breast tissue, prostate tissue, lymph node tissue and lung tissue.

6. The method of claim 1, wherein the machine learning predictor model comprises a generative adversarial network.

7. The method of claim 1, wherein the machine learning predictor model comprises a self-supervised learning neural network.

8. The method of claim 1, wherein the machine learning predictor model comprises a convolutional neural network.

9. The method of claim 1, wherein the machine learning predictor model comprises a convolutional neural network for dense segmentation.

10. A system comprising:
    a non-transitory computer-readable medium; and
    one or more processors communicatively coupled to the non-transitory computer-readable medium, the one or more processors configured to execute processor-executable instructions stored in the non-transitory computer-readable medium to:
    obtain an input red-green-blue ("RGB") image of a tissue specimen;
    supply the input RGB image to a machine learning predictor model trained from a multitude of pairs of aligned RGB images of tissue specimens, one of the RGB images of the pair of RGB images comprising an RGB image of a tissue specimen stained with a special stain, the model trained to predict an RGB image of a tissue specimen stained with the special stain;
    use the predictor model to generate a predicted RGB image of the tissue specimen stained with the special stain; and
    output the predicted RGB image as a virtual RGB image.

11. The system of claim 10, wherein the input RGB image comprises an image of the tissue specimen in an unstained condition.

12. The system of claim 10, wherein the input RGB image comprises an image of the tissue specimen stained with a routine stain.

13. The system of claim 10, wherein the special stain comprises an IHC stain.

14. The system of claim 10, wherein the tissue specimen is of one of the following types: breast tissue, prostate tissue, lymph node tissue and lung tissue.

15. The system of claim 10, wherein the machine learning predictor model comprises a generative adversarial network.

16. The system of claim 10, wherein the machine learning predictor model comprises a self-supervised learning neural network.

17. The system of claim 10, wherein the machine learning predictor model comprises a convolutional neural network.

18. The system of claim 10, wherein the machine learning predictor model comprises a convolutional neural network for dense segmentation.

19. A non-transitory computer-readable medium comprising processor-executable instructions configured to cause one or more processors to:
    obtain an input red-green-blue ("RGB") image of a tissue specimen;
    supply the input RGB image to a machine learning predictor model trained from a multitude of pairs of aligned RGB images of tissue specimens, one of the RGB images of the pair of RGB images comprising an RGB image of a tissue specimen stained with a special stain, the model trained to predict an RGB image of a tissue specimen stained with the special stain;
    use the predictor model to generate a predicted RGB image of the tissue specimen stained with the special stain; and
    output the predicted RGB image as a virtual RGB image.

* * * * *